(12) United States Patent
Seitz et al.

(10) Patent No.: US 11,583,325 B2
(45) Date of Patent: Feb. 21, 2023

(54) SCREW DRIVE HAVING INTEGRATED TORQUE SECURITY

(71) Applicant: Syntellix AG, Hannover (DE)

(72) Inventors: Jan Marten Seitz, Hannover (DE); Ute Urban, Hannover (DE); Nils Heinemann, Hannover (DE)

(73) Assignee: Syntellix AG, Hannover (DE)

( * ) Notice: Subject to any disclaimer, the term of this patent is extended or adjusted under 35 U.S.C. 154(b) by 836 days.

(21) Appl. No.: 16/340,997

(22) PCT Filed: Oct. 6, 2017

(86) PCT No.: PCT/EP2017/075531
§ 371 (c)(1),
(2) Date: Jan. 22, 2020

(87) PCT Pub. No.: WO2018/069190
PCT Pub. Date: Apr. 19, 2018

(65) Prior Publication Data
US 2020/0205871 A1 Jul. 2, 2020

(30) Foreign Application Priority Data
Oct. 10, 2016 (DE) .................... 10 2016 119 234.1

(51) Int. Cl.
*A61B 17/86* (2006.01)
*A61B 90/00* (2016.01)

(52) U.S. Cl.
CPC .... *A61B 17/8615* (2013.01); *A61B 2090/031* (2016.02)

(58) Field of Classification Search
CPC ...... F16D 1/101; F16B 23/003; F16B 41/005; F16B 23/0038; F16B 23/0092; F16B 31/021; F16B 31/027; F16B 31/02; B25B 13/485; A61B 2090/037; A61B 17/8615
See application file for complete search history.

(56) References Cited

U.S. PATENT DOCUMENTS

| | | | | |
|---|---|---|---|---|
| 1,910,182 A | * | 5/1933 | Robertson | F16B 23/0092 411/410 |
| 3,763,725 A | * | 10/1973 | Reiland | F16B 31/021 81/124.6 |
| 3,865,007 A | * | 2/1975 | Stanback | F16B 23/0007 439/814 |
| 3,888,144 A | * | 6/1975 | Parsons | F16B 23/0015 81/436 |
| 5,020,954 A | * | 6/1991 | Dreger | F16B 23/0023 411/404 |
| 5,358,368 A | * | 10/1994 | Conlan | F16B 23/0092 411/410 |

(Continued)

OTHER PUBLICATIONS

European Patent Office, International Search Report, dated Dec. 21, 2017, World Intellectual Property Organization, Rijswijk.

*Primary Examiner* — David W Bates
(74) *Attorney, Agent, or Firm* — Dennemeyer & Associates, LLC (57) ABSTRACT

The present invention relates to a screw drive having integrated torque protection, wherein two screw drives are incorporated in a screw head, one drive being an internal polygonal drive and the second drive being an internal multilobular drive. In addition, the invention relates to a screw having a screw drive.

8 Claims, 10 Drawing Sheets

(56) References Cited

U.S. PATENT DOCUMENTS

| | | | | |
|---|---|---|---|---|
| 6,293,745 | B1* | 9/2001 | Lu | F16B 23/0053 |
| | | | | 411/404 |
| 6,328,517 | B1* | 12/2001 | Mann | F16B 23/0038 |
| | | | | 411/404 |
| 6,890,139 | B2* | 5/2005 | Hughes | B25B 15/005 |
| | | | | 411/410 |
| 8,992,544 | B2* | 3/2015 | Sasing | A61B 17/7077 |
| | | | | 606/104 |
| 10,100,864 | B2* | 10/2018 | Rathmann | F16B 23/003 |
| D883,765 | S* | 5/2020 | Schwartzkopf | D8/86 |
| 10,995,788 | B2* | 5/2021 | Dilling | B21K 1/463 |
| 11,058,469 | B2* | 7/2021 | Mahajan | A61B 17/8605 |
| 2005/0098000 | A1* | 5/2005 | Brooks | F16B 23/0038 |
| | | | | 81/439 |
| 2006/0266168 | A1* | 11/2006 | Pacheco | B25B 15/005 |
| | | | | 81/460 |
| 2009/0129887 | A1* | 5/2009 | Chang | B25B 13/485 |
| | | | | 411/402 |
| 2009/0198291 | A1* | 8/2009 | Kevin | A61B 17/863 |
| | | | | 606/305 |
| 2014/0241826 | A1* | 8/2014 | Caponera | F16B 35/042 |
| | | | | 470/8 |
| 2014/0257408 | A1* | 9/2014 | Trieu | A61B 17/8615 |
| | | | | 606/301 |
| 2015/0335368 | A1 | 11/2015 | Auger et al. | |
| 2016/0160902 | A1* | 6/2016 | Tamm | F16B 31/021 |
| | | | | 411/3 |
| 2016/0262819 | A1 | 9/2016 | May et al. | |
| 2018/0347612 | A1* | 12/2018 | Falkenstein | F16B 23/003 |
| 2019/0003510 | A1* | 1/2019 | Chasse | F16B 23/003 |

\* cited by examiner

SCREW DRIVE HAVING INTEGRATED TORQUE SECURITY

CROSS-REFERENCE TO RELATED APPLICATIONS

This is a 35 U.S.C. 371 National Stage Patent Application of International Application No. PCT/EP2017/075531, filed Oct. 6, 2017, which claims priority to German application 10 2016 119 234.1, filed Oct. 10, 2016, each of which is hereby incorporated by reference in its entirety.

DESCRIPTION

The present invention relates to a screw drive having integrated torque protection, and a screw having a screw drive.

The screw drive is designed such that mechanical overloading of the screw is avoided when being screwed into a material, which could result in the screw head breaking off, the screw shearing in the shaft or the thread being overtightened and torn out.

When using screws, it is easy for the screw to become damaged by an excessive mechanical load, which makes further screwing of the screw into a material or removal of the screw from the material difficult or even impossible.

Screws are used in many different fields.

Nowadays, screws made of biodegradable magnesium alloys can be used for osteosynthesis in bone fractures or for the surgical correction of malpositions and deformations of bones, for example in hallux valgus (bunion), hammertoes, but also in fractures of the radius or ulna, in fractures of the upper arm or shoulder, and fractures of the tarsal bones (Luthringer, J. C., Feyerabend F., Willumeit-Römer, R.—Magnesium Based Implants: A Mini Review, Magnesium Research 2014 (4) 142-154). These special magnesium materials have a strength comparable to that of human bone to allow for very stable and durable connections of bone fragments to be joined together. This ensures quick and reliable healing of a bone fracture or a misalignment of bones. At the same time, the body can resorb the magnesium material, screwed into the bone in the form of a screw, over the course of about one year and, to a large extent, even convert it into the body's own bone substance. After the fracture has healed, the screw used to fix bone parts need not be removed in a second operation as required when using non-degradable titanium or stainless steel screws. Rather, the magnesium screw introduced is gradually dissolved to form magnesium ions. Some of the magnesium ions are excreted in the urine by the kidneys, while some of it is also incorporated in the bone itself into the new bone substance that is forming.

The tensile and breaking strength of biodegradable magnesium alloys is above the tensile and breaking strength of human bone. The literature contains information on the tensile strength of human bone of 80 to 150 MPa and elastic moduli of 10 to 35 GPa (Wintermantel, E. and Ha, S.-W. in Biokompatible Werkstoffe and Bauweisen, Springer, Heidelberg—New York, 1996). The tensile strength values of biodegradable magnesium alloys range from 100 MPa to 400 MPa and from 40 GPa to 50 GPa for the elastic modulus. For this reason, biodegradable magnesium materials are therefore ideally suited for osteosynthesis because they are close to the strength of bone.

Biodegradable magnesium alloys are therefore also more advantageous than polymer-based biodegradable materials which do not have this strength. Advantages in comparison with screws made of high-strength metals, such as titanium or stainless steel, arise from the fact that implants made from these materials often have to be removed in a second operation after healing, which is not the case with biodegradable magnesium materials. In addition, when using materials such as steel or titanium, the strength of which is far above that of bone, an undesirable stress shielding effect is observed, hampering healing and, in the worst case, may even result in bone loss around the implant (B. Daniels et al., Journal of Applied Biomaterials 1/1 (1990), pages 57-98).

During operations for the osteosynthesis of a broken bone or after surgical correction of deformed bones, the surgeon will reposition the parts of the bone to be joined together and securely fix them with a screw. The screw is generally screwed into a channel pre-drilled into the bone and optionally pre-cut with a thread. A sterile biodegradable magnesium screw is screwed in using a special sterile screwdriver.

When screwing in the screw, the following complications can occur.

On the one hand, the screw can jam, perhaps because the pre-drilled channel is too tight or too short or because a thread has not been pre-cut properly. There is a risk that the surgeon turns the head of the magnesium screw too tightly and thereby breaks off or shears off the screw head or even causes a shaft fracture. If the screw has not been completely screwed in, fixation of the fracture is not ensured. The screw would have to be removed again, which is difficult with a broken screw head and can only be done with special tools. Under certain circumstances, additional surgical intervention and, in some cases, removal by drilling out the implant may become necessary. The procedures mentioned are time-consuming, and the operation would in any case take become significantly protracted.

In addition, it is also possible for the surgeon to have fixed the fracture perfectly and fully screwed in the magnesium screw. Then the screw has to be tightened to produce an optimal frictional connection between the bone fragments. In the process, there is a risk of the screw becoming over-tightened in the thread and tearing off if its holding force is exceeded. The frictional connection would break down; the screw would only provide a loose connection of the bone fragments. In this situation, the surgeon must decide based on feeling whether the screw is optimally seated or whether it is already over-tightened. In addition, by excessive tightening of the screw, the previously described complication can also occur, such as the case of the screw head breaking off.

In all these situations, costly and time-consuming prolongation of the surgery time may result.

In other fields where screws are used, such as in electronic and precision mechanical components, watches, toys, furniture, household electrical appliances, sports equipment, it is possible for the screw drive to be damaged by excessive mechanical stress so that further screwing in or removal of the screw is hampered or even prevented.

For example, screws having two screw drives are known from US 2016/0262819 A1, US 2015/0335368 A1, and US 2014/0257408 A1. One drive is an internal polygonal drive, and the second drive is an internal multilobular drive in the form of a multi-ray star, in which the rays are formed in the shape of rounded points or other shapes of the points.

The aim of the present invention is to provide a screw drive which makes it possible to screw the screw further into or out of the material despite damage to the drive.

The aim is achieved by the screw drive according to the invention according to claim 1.

A screw drive having integrated torque protection is preferred, wherein two screw drives are incorporated in a screw head, wherein one drive is an internal polygonal drive and the second drive is an internal multilobular drive.

For this purpose, two combined screw drives are incorporated in the screw head, wherein one drive is an internal polygonal drive, allowing reverse rotation of the screw, and the second drive is an internal multilobular drive, which is designed such that, when a torque adapted to the design of the screw is exceeded, the points enabling the drive break off, shear or are pressed flat to prevent damage to the thread and the screw shaft, or prevent the screw head being torn off.

The screw drive according to the invention thus has structural, integrated torque protection, which prevents the screw head from breaking off, the screw head or the shaft from shearing, the thread from tearing out or the screw from being over-tightened in the bone channel, and other damage possible by overloading the screw, and enables easy removal of the screw after any overloading.

The present invention also relates to attaching the internal multilobular drive to the internal polygonal drive such that, after points of the internal multilobular drive break off on account of the maximum torque being exceeded, the polygonal internal drive is preserved. Breaking of the points in the context of the present invention means any breaking off or shearing of the points on account of the maximum torque being exceeded.

It is advantageous if the points of the internal multilobular drive are in one plane with the internal polygonal drive. The points of the internal multilobular drive then lie directly on the edges of the internal polygonal drive and in one plane with the same.

The drive tool, a special internal multilobular screwdriver, then slips through in the screw head and can no longer transfer any force or torque to the screw. The height of the points remaining after breaking is generally in the range of fractions of a millimetre. The point remnants do not impede the use of an internal polygonal screwdriver, by means of which the screw can be unscrewed again.

In a further advantageous embodiment, the internal polygonal drive is laid deeper in the screw than the internal multilobular drive. The points of the internal multilobular drive are then not in a plane with the edges of the internal polygonal drive, but above them.

It may also be preferred for the internal polygonal drive to have a smaller diameter than the internal multilobular drive. The diameter for the internal multilobular drive is to be understood as the circle that is tangent to the points inside at its base (H). The diameter for the internal polygonal drive is to be understood as the circle which is tangent to all edges (B). The screw drive according to the invention is suitable in the field of osteosynthesis, in particular for biodegradable magnesium screws, but not limited to this use. By means of the screw drive according to the invention in the head of a screw, preferably of a biodegradable magnesium screw, the rotational movement applied by a tool is reliably transmitted to the screw. Other biodegradable materials, such as polymers, are also suitable for this drive and the corresponding screw.

However, the screw drive according to the invention is not limited to the field of osteosynthesis. Any other applications and materials of screws that allow the points to break off, such as metals or wood, are included as well. In a preferred embodiment, the screw drive according to the invention consists of at least one polymer or of wood or of ceramic or of a composite or of at least one metal.

The points sheared off when the torque protection is triggered or the fragments thereof pose no risk to the patient in the field of osteosynthesis since they consist of a biodegradable material. Provided that abrasions or fragments are not flushed out, collected and removed, they can remain in the region of the surgical wound without concern since, like the screw implant itself, they are completely absorbed or degraded by the body. The biodegradable magnesium alloys do not pose a burden on the physiological system. The advantage of the design of the screw drive according to the invention is that, in the case of complications during surgery, the screws can be removed and appropriate corrections can be made very quickly and safely, with the simplest means.

Within the context of the present invention, an internal polygonal drive is preferably understood to mean an internal hexagonal drive, for example a hexagon socket screw. The internal polygonal drive is designed as an internal hexagonal drive or as an internal pentagonal drive or as an internal square drive or as an internal triangular drive or as an internal octagonal drive. Other internal polygonal drives comprising a different number of edges can also be advantageous.

In the context of the present invention, an internal multilobular drive is understood to mean a screw drive in the form of a multi-point star in which the rays (points) are rounded. It can be a six-pointed star (internal hexalobular, Torx®) or else an internal pentalobular drive or internal quadlobular or internal trilobular drive or internal octolobular drive. Other internal multilobular drives having a different number of points and other shapes of the points can also be advantageous.

Instead of the rounded points, triangular points, square points (with or without chamfers), semi-circular points or oval points can be used as over-tightening protection.

To ensure very low torques, individual points can be omitted. For example, instead of the 6 points on a hexagon socket profile, just 3 points can be used.

In addition, the points can be selectively weakened to adapt the maximum torque particularly finely and precisely to the overall design of the screw. This is achieved by drilled holes introduced into the points. It is therefore further preferred that the torque protection points of the internal multilobular drive are selectively weakened by a drilled hole or a plurality of drilled holes so that even very small torques lead to triggering of the screw protection by the points breaking off.

According to a further aspect of the present invention, the diameter of the internal hexagon drive (B) is 1-20 mm, preferably 3 mm, the depth of the screw drive (C) is 0.5-6 mm, preferably 2.5 mm, the thickness of the torque protection points at the base (F) is 0.1-4 mm, preferably 0.5 mm, the height of the torque protection points (G) is 0.1-3 mm, preferably 0.5 mm, the residual height of the points after breaking off or shearing (G*) is 0.01-1 mm, preferably 0.1 mm, and the diameter of the drilled hole in the point for weakening the maximum torque (2R) is 0.06-1.6 mm, preferably 0.2 mm.

In a preferred embodiment, the screw drive according to the invention consists of a magnesium alloy comprising a rare earth metal content of 1.5 to 5% by weight, preferably 1.5 to 2.5% by weight of neodymium, an yttrium content of 1.5 to 5% by weight, a zirconium content of 0.1 to 2.5% by weight, a zinc content of 0.01 to 1% by weight, as well as unavoidable impurities, wherein the total content of any impurities is below 1% by weight and the aluminium content is less than 0.5% by weight, and the remainder up to 100% by weight is magnesium.

In most cases, the screw drive consists of about 80% by weight of magnesium, usually about 90% by weight of magnesium and the alloying elements calcium, lithium, zinc, scandium, yttrium, lanthanum and rare earth metals, especially neodymium, cerium, dysprosium, and other SE metals. Titanium, zirconium, manganese, or silver can also be alloyed in smaller quantities. In contrast, elements such as copper, aluminium, iron, nickel, and phosphorus should be regarded as rather harmful impurities and should advantageously be present in the biodegradable alloys only in concentrations below 0.1% by weight. This alloy has a tensile strength of about 300 MPa.

The torque-protected screw drive according to the invention is preferably produced by filigree milling from a screw blank. Alternatively, the screw head having the torque-protected drive according to the invention can also be manufactured by mechanical pressing of a blank in a corresponding mould or by the method of die-casting. For some materials, e. g. for plastics or polymeric materials, the method of 3D printing may also be used.

It is further preferred that the torque at which the torque protection of the screw drive according to the invention occurs by shearing of the protection points is 0.28 Nm for a screw having a
 diameter of the screw head (A) of 4 mm, a
 diameter of the internal polygonal drive (B) of 2.12 mm, a
 depth of the screw drive (C) of 1.2 mm, a
 diameter of the screw shaft/thread diameter (D) of 2 mm, a
 total length of the screw (E) of 6-20 mm, a
 thickness of the torque protection point at the base (F) of 0.322 mm, and
 a height of the torque protection points (G) of 0.211 mm.

It is also preferred that the torque at which the torque protection of the screw drive according to the invention occurs by shearing of the protection points is 0.67 Nm for a screw having a
 diameter of the screw head (A) of 5 mm, a
 diameter of the internal polygonal drive (B) of 2.06 mm, a
 depth of the screw drive (C) of 1.6 mm, a
 diameter of the screw shaft/thread diameter (D) of 2.7 mm, a
 total length of the screw (E) of 6-30 mm, a
 thickness of the torque protection point at the base (F) of 0.4 mm, and
 a height of the torque protection points (G) of 0.3 mm.

Furthermore it is advantageous that the torque at which the torque protection of the screw drive according to the invention occurs by shearing of the protection points is 1.42 Nm for a screw having a diameter of the screw head (A) of 6 mm, a
 diameter of the internal polygonal drive (B) of 2.62 mm, a
 depth of the screw drive (C) of 1.8 mm, a
 diameter of the screw shaft/thread diameter (D) of 3.5 mm, a
 total length of the screw (E) of 8-40 mm, a
 thickness of the torque protection points at the base (F) of 0.4 mm and a
 height of the torque protection points (G) of 0.27 mm.

Furthermore, the aim is achieved by a screw having a screw drive. By means of the screw drive according to the invention in the head of the screw, the rotational movement applied by a tool is reliably transmitted to the screw.

This screw drive is suitable in the field of osteosynthesis, in particular for biodegradable magnesium screws, but not limited to this use. Other biodegradable materials, such as polymers, are also suitable for this drive and the corresponding screw.

The screw drive according to the invention and the screw according to the invention are not limited to the field of osteosynthesis. Any other applications and materials of screws that allow the points to break off, such as metals or wood, are included as well.

In a preferred embodiment, the screw drive according to the invention and/or the screw consist of at least one polymer or of wood or of ceramic or of composite or of at least one metal. The screw and screw drive can also consist of different materials, therefore do not have to be manufactured of the same material.

In a preferred embodiment, a biodegradable magnesium screw and the screw drive consists of a magnesium alloy comprising a rare earth metal content of 1.5 to 5% by weight, preferably 1.5 to 2.5% by weight of neodymium, an yttrium content of 1.5 to 5% by weight, a zirconium content of 0.1 to 2.5% by weight a zinc content of 0.01 to 1% by weight as well as unavoidable impurities, wherein the total content of any impurities is below 1% by weight and the aluminium content is less than 0.5% by weight, and the remainder up to 100% by weight is magnesium.

In most cases, the screw and the screw drive consist of about 80% by weight of magnesium, usually about 90% by weight of magnesium and the alloying elements calcium, lithium, zinc, scandium, yttrium, lanthanum and rare earth metals, especially neodymium, cerium, dysprosium, and other SE metals. Titanium, zirconium, manganese, or silver can also be alloyed in smaller quantities. In contrast, elements such as copper, aluminium, iron, nickel and phosphorus should be regarded as rather harmful impurities and should be present in the biodegradable alloys only in concentrations below 0.1% by weight.

This alloy has a tensile strength of about 300 MPa.

The torque-protected screw drive according to the invention is preferably produced by filigree milling from a screw blank. Alternatively, the screw head having the torque-protected drive according to the invention can also be manufactured by mechanical pressing of a blank in a corresponding mould or by the method of die-casting. In an advantageous embodiment, the method of 3D printing is provided for suitable materials.

It is advantageous if the points of the internal multilobular drive are in one plane with the internal polygonal drive. The points of the internal multilobular drive then lie on the edges of the internal polygonal drive and in one plane with the same.

In a further advantageous embodiment, the internal polygonal drive is laid deeper in the screw than the internal multilobular drive. The points of the internal multilobular drive are then not in a plane with the edges of the internal polygonal drive, but above them.

It may also be preferred for the internal polygonal drive to have a smaller diameter than the internal multilobular drive. The diameter for the internal multilobular drive is to be understood as the circle that is tangent to the points inside at its base (H). The diameter for the internal polygonal drive is to be understood as the circle which is tangent to all edges (B).

According to another aspect of the present invention, the
diameter of the screw head (A) is 2-30 mm, preferably 6 mm, the diameter of the hexagon drive (B) is 1-20 mm, preferably 3 mm, the depth of the screw drive (C) is 0.5-6 mm, preferably 2.5 mm, the diameter of the screw shaft/thread diameter (D) is 2-15 mm, preferably 3.5 mm, the total length of the screw (E) is 5-120 mm, preferably 30 mm, the thickness of the torque protection points at the base (F) is 0.1-4 mm, preferably 0.5 mm, the height of the torque protection points (G) is 0.1-3 mm, preferably 0.5 mm, the residual height of the points after breaking off or shearing (G*) is 0.01-1 mm, preferably 0.1 mm, and the diameter of the drilled hole in the point for weakening the maximum torque (2 R) is 0.06-1.6 mm, preferably 0.2 mm.

It is further preferred that the torque at which the torque protection of the screw drive according to the invention occurs by shearing of the protection points is 0.28 Nm for a screw having a diameter of the screw head (A) of 4 mm, a diameter of the internal polygonal drive (B) of 2.12 mm, a depth of the screw drive (C) of 1.2 mm, a diameter of the screw shaft/thread diameter (D) of 2 mm, a total length of the screw (E) of 6-20 mm, a thickness of the torque protection points at the base (F) of 0.322 mm and a height of the torque protection point (G) of 0.211 mm.

It is also preferred that the torque at which the torque protection of the screw drive according to the invention occurs by shearing of the protection points is 0.67 Nm for a screw having a diameter of the screw head (A) of 5 mm, a diameter of the internal polygonal drive (B) of 2.06 mm, a depth of the screw drive (C) of 1.6 mm, a diameter of the screw shaft/thread diameter (D) of 2.7 mm, a total length of the screw (E) of 6-30 mm, a thickness of the torque protection point at the base (F) of 0.4 mm and a height of the torque protection point (G) of 0.3 mm.

Furthermore it is advantageous that the torque at which the torque protection of the screw drive according to the invention occurs by shearing of the protection points is 1.42 Nm for a screw having a diameter of the screw head (A) of 6 mm, a diameter of the internal polygonal drive (B) of 2.62 mm, a depth of the screw drive (C) of 1.8 mm, a diameter of the screw shaft/thread diameter (D) of 3.5 mm, a total length of the screw (E) of 8-40 mm, a thickness of the torque protection points at the base (F) of 0.4 mm and a height of the torque protection point (G) of 0.27 mm.

BRIEF DESCRIPTION OF THE FIGURES

The present invention is explained in more detail with reference to the following figures.

DETAILED DESCRIPTION OF THE FIGURES

Figure 1:
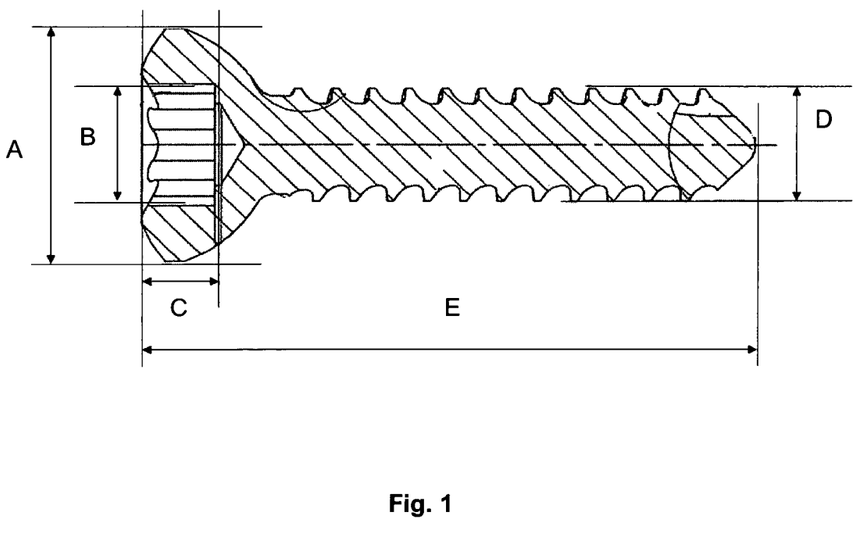
FIG. 1 Longitudinal section of a magnesium screw for osteosynthesis

Designs for implementing the invention are shown in FIGS. 1 to 9. These refer to the example of osteosynthesis for illustrative purposes; however, the present invention is not limited to this field. FIG. 1 shows the typical longitudinal section through a magnesium screw according to the invention, as used in osteosynthesis. Various variants of the screw drive according to the invention and the screw having a screw drive according to the invention are shown in FIGS. 2 to 9.

Figure 2:
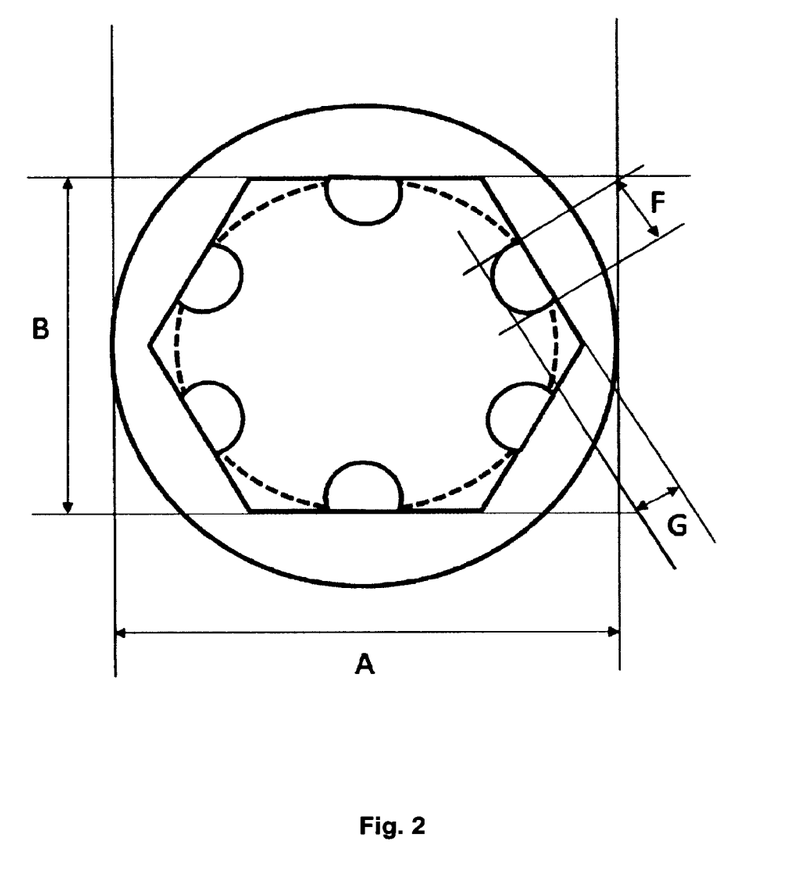
FIG. 2 Principle of the screw head according to the invention in a design with internal hexagon socket and six internal points that limit the torque FIG. 3 Top view of a screw head according to the invention according to FIG. 2 after the maximum torque is exceeded FIG. 4 Top view of a screw head according to the invention with internal hexagon socket and six internal points that limit the torque FIG. 5 Principle of the screw head according to the invention in which the torque protection points are incorporated in an internal square FIG. 6 Top view as in FIG. 5, but after shearing of the points ensuring the maximum torque FIG. 7 Principle sketch of a torque-protected screw head having triangular points FIG. 8 Particularly advantageous torque-protected screw head of a magnesium screw according to the invention having six internal points that limit the torque to 1.42 Nm FIG. 9 Torque-protected screw head of a magnesium screw according to the invention having six internal points, wherein drilled holes with radius R in the points bring about targeted weakening for adapting the torque to the structural design of the screw FIG. 10 Embodiment in which the internal polygonal drive is laid deeper in the screw than the internal multilobular drive
Figure 3:
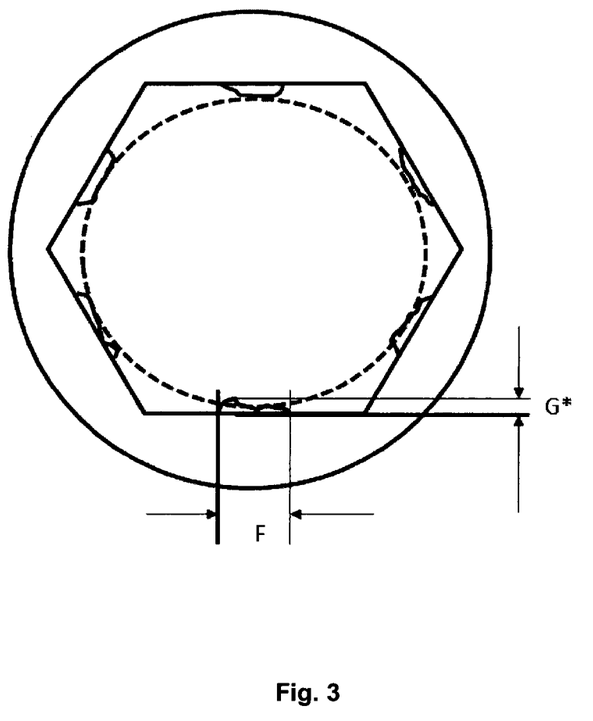

The principle of the invention in the embodiment in which the points of the internal multilobular drive lie in one plane with the internal polygonal drive is shown in FIGS. 2 and 3.

An internal hexalobular drive is incorporated in the form of a screw drive in the head of the screw consisting of a biodegradable magnesium material with 3 to 6, preferably 6 points, wherein the points are placed on the edges of a hexagon drive (hexagon socket screw), effectively behind it. F and G mark the width and thickness of the points, A marks the diameter of the screw head, and B marks the diameter of the hexagon profile to which the points are attached.

Figure 4:
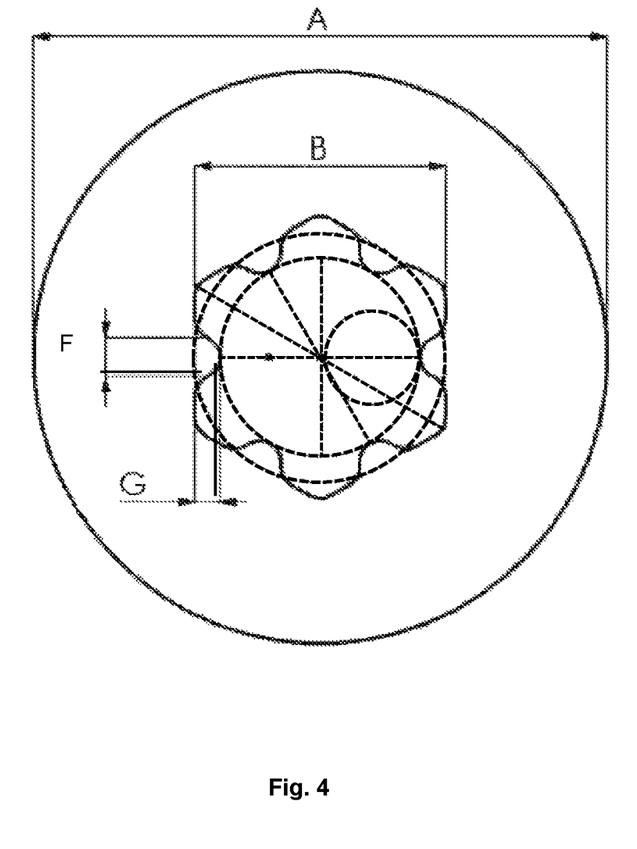

FIG. 4 shows the drive of a magnesium screw, in which the torque protection according to the invention is implemented in a Torx design according to DIN EN ISO 10664 on a hexagon socket screw.

The dimensions of the Torx points are structurally designed such that they shear, tear or push away to the side when excessive force is applied to them or when torque is applied to them that is large enough that there is a risk of the entire head of the magnesium screw breaking off or shearing, or if a torque acts on the screw head that exceeds the pressing force/holding force of the screw.

In this case, the points of the Torx drive break off or are pressed away to the side even before the screw or thread is damaged. The drive tool, a special Torx screwdriver, then slips through in the screw head and can no longer transfer any force or torque to the screw. The design can be referred to as "integrated torque protection in the screw head". The situation that occurs after shearing of the Torx points is shown schematically in FIG. 3 and FIG. 6. G* accordingly indicates the height of the points that remain after breaking off. It is generally in the range of fractions of a millimetre. The point remnants do not impede the use of a hexagon socket screwdriver, by means of which the screw can be unscrewed again.

If the torque protection has been triggered, i.e. the Torx points have been sheared off, the screw can no longer be turned using the Torx driver. However, it can still be unscrewed and thus easily and safely removed by means of the integrated hexagonal drive, on which the Torx points have been placed and which is preserved during this process. This can also be seen from FIG. 3. After surgical correction of the bone canal, a new, possibly stronger, shorter, or altogether differently designed, biodegradable screw can then be inserted.

The points sheared when the torque protection is triggered or the fragments thereof pose no risk to the patient since they consist of a biodegradable material. Provided that abrasions or fragments are not flushed out, collected and removed, they can remain in the region of the surgical wound without concern since, like the screw implant itself, they are completely absorbed or degraded by the body. The biodegradable magnesium alloys do not pose a burden on the physiological system.

The advantage of the design of the screw drive according to the invention is that, in the case of complications during surgery, the screws can be removed and appropriate corrections can be made very quickly and safely, with the simplest means. This is also the case for screws in other applications.

Figure 5:
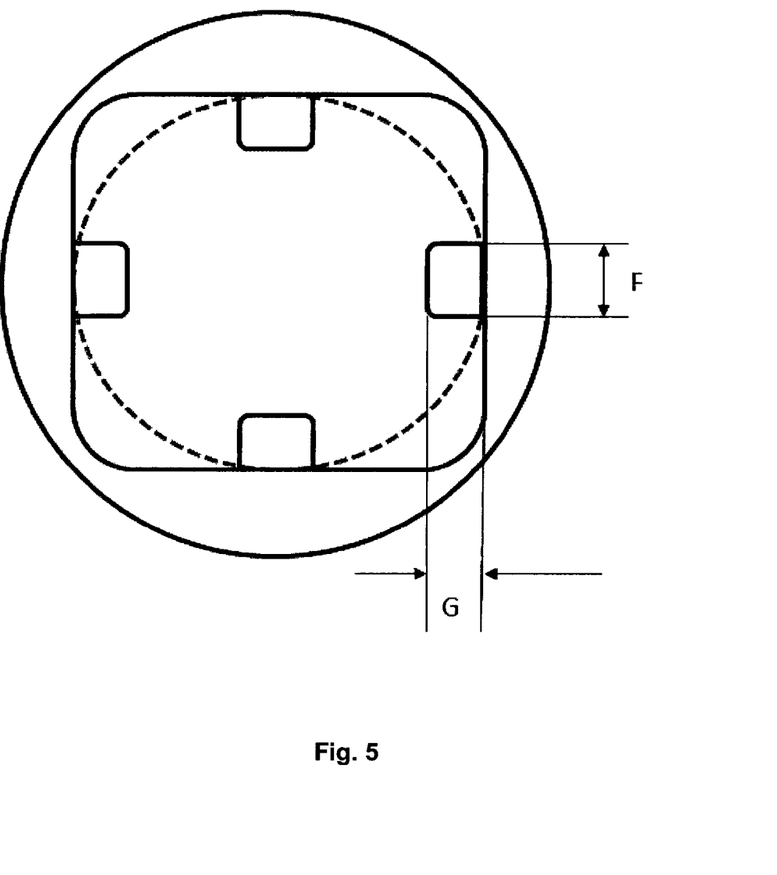
Figure 6:
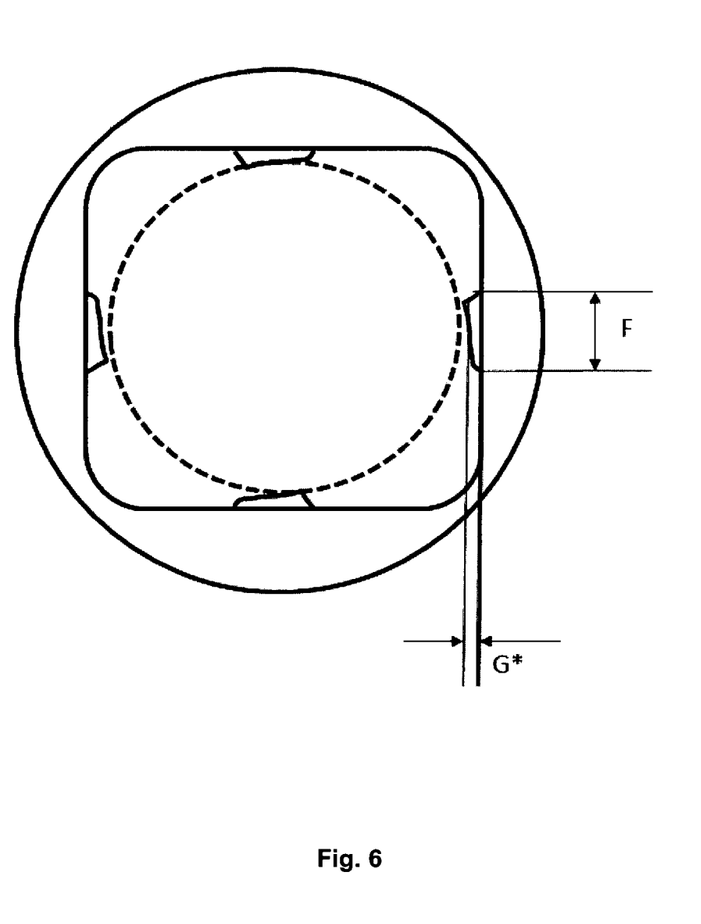
Figure 7:
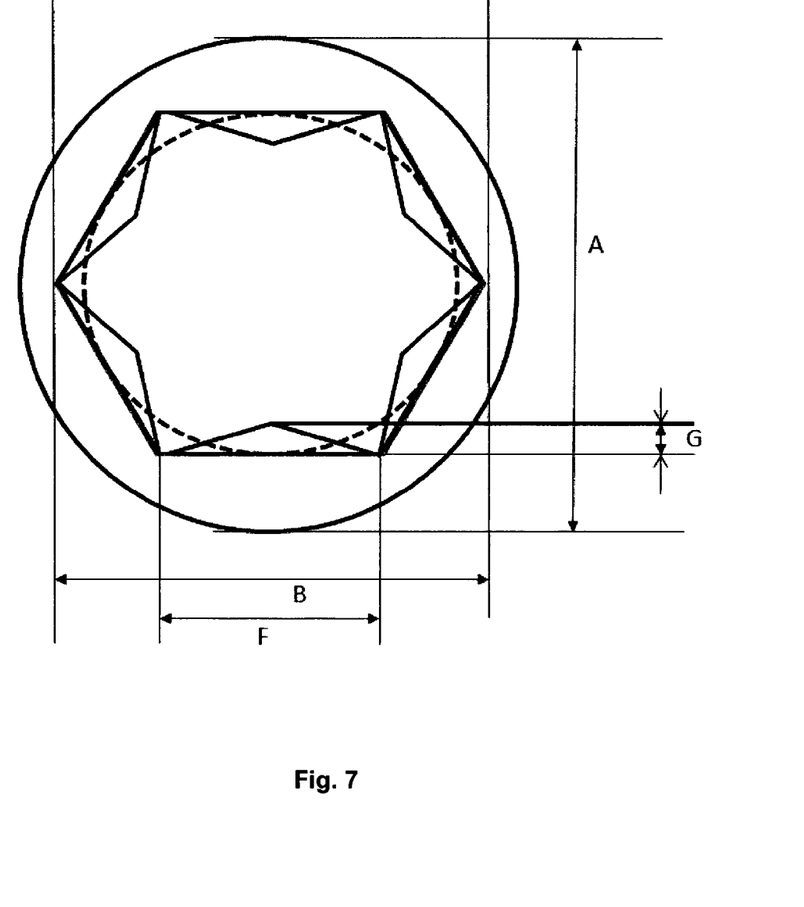

The invention is not constrained to a screw head having a hexagon socket. The points that limit torque can also be machined to an internal square socket, triangular socket, or octagonal socket screw head. FIGS. 5 and 6 show the principle of a design having an internal square drive and attached points before and after the shearing of the points when the screw overloaded. It is also not necessary to set a torque limit with Torx points that correspond precisely to the ISO standard. Instead, it is also possible to use triangular points (FIG. 7), square points (FIG. 6)—with or without chamfers—semi-circular points (FIG. 2) or oval points as over-tightening protection.

To ensure very low torques, individual points can be omitted. For example, instead of the 6 points on a hexagon socket profile, just 3 points can be used.

Figure 9:
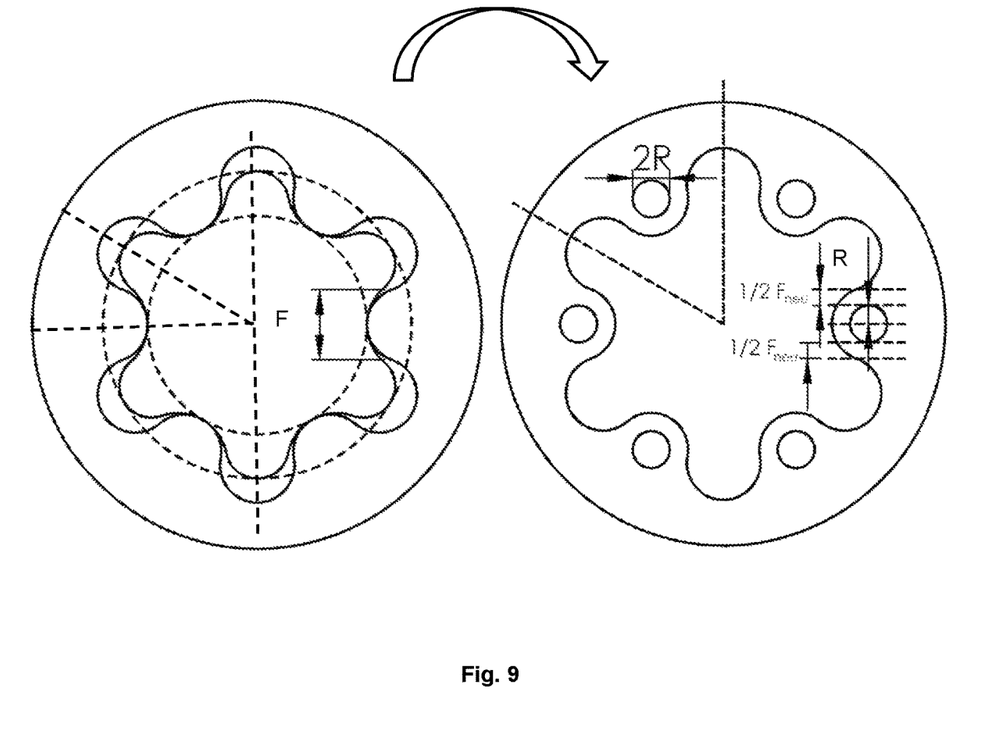

In addition, the points can be selectively weakened to adapt the maximum torque particularly finely and precisely to the overall design of the screw. This is achieved by drilled holes introduced into the points. FIG. 9 shows this possibility by way of example of an internal hexalobular screw head. By means of drilled holes with radius R, the thickness F of the point is weakened the base. The larger R, the greater the weakening of the point. The thickness of the point at the base is reduced from F to $F_{new}=F-2R$. The torque at which the points break off can thus be selectively reduced. With this detailed design, the torque protection according to the invention can be adapted to biodegradable magnesium screws of all types and dimensions, to all conceivable thread types and also to magnesium materials of various strengths, as well as to any other materials, such as plastics, wood, metal or alloys of all kinds.

The torque-protected screw drives according to the invention are preferably produced by filigree milling the forms (shown in more detail in the drawings) from a screw blank. Alternatively, the screw head having the torque-protected drive according to the invention can also be manufactured by mechanical pressing of a blank in a corresponding mould or by the method of die-casting. Any desired material can be used as a material for the blank Biodegradable magnesium alloy can be used for the field of osteosynthesis, but it is preferable to use an alloy consisting of 1.5 to 5% by weight of rare earths, including 1.5 to 2.5% by weight of neodymium, 1.5 to 5.0% by weight of yttrium, 0.01 to 1.0% by weight of zinc, 0.1 to 2.5% by weight of zirconium, the remainder being magnesium, wherein the contents of impurities of Al, Si, Ni, and Fe are each below 0.5% by weight.

Figure 8:
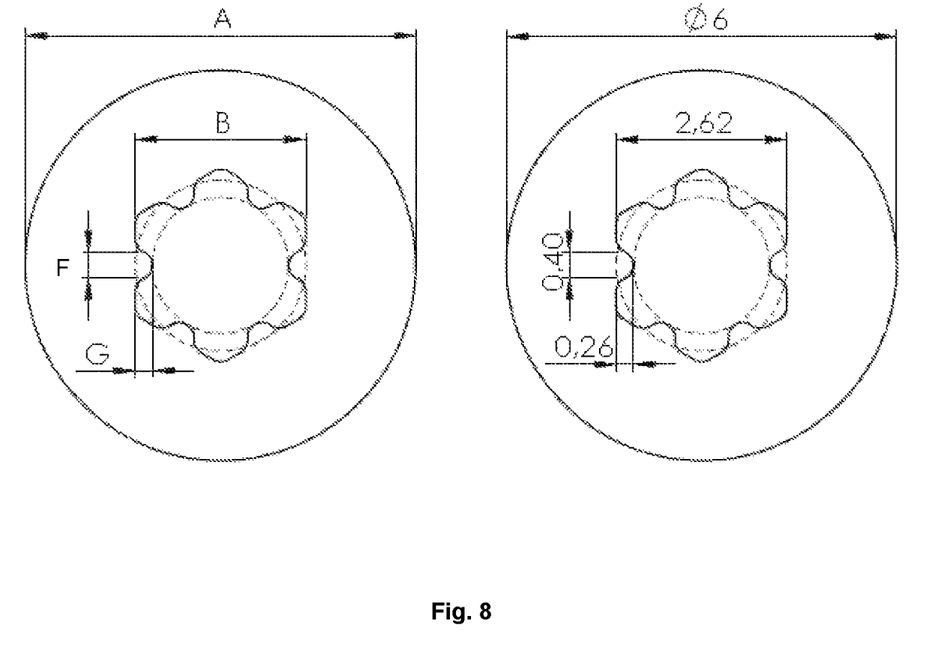

A particularly advantageous embodiment of the invention is shown in FIG. 8. It relates to a screw made of a magnesium alloy consisting of 1.5 to 5% by weight of rare earths, including 1.5 to 2.5% by weight of neodymium, 1.5 to 4.0% by weight of yttrium, 0.01 to 1.0% by weight of zinc, 0.2 to 2.0% by weight of zirconium, the remainder being magnesium. Shown is the torque-protected screw drive of a screw according to FIG. 1, having the dimensions A=6.0 mm, B=2.62 mm, C=1.8 mm, D=3.5 mm, E=8.0 to 40 mm. In the screw head, an internal hexagon drive of B=2.62 mm is incorporated, on the edges of which Torx points of dimensions F=0.40 mm and G=0.26 mm are placed. The points lie in one plane with the internal hexagonal drive and are attached to its edges. This screw head is torque-protected at a torque of 1.42+/−0.12 Nm. If this torque is exceeded, the points break off and the screw cannot be damaged any further. It can then be unscrewed from the bone using a suitable hexagon socket and replaced with another screw.

Figure 10:
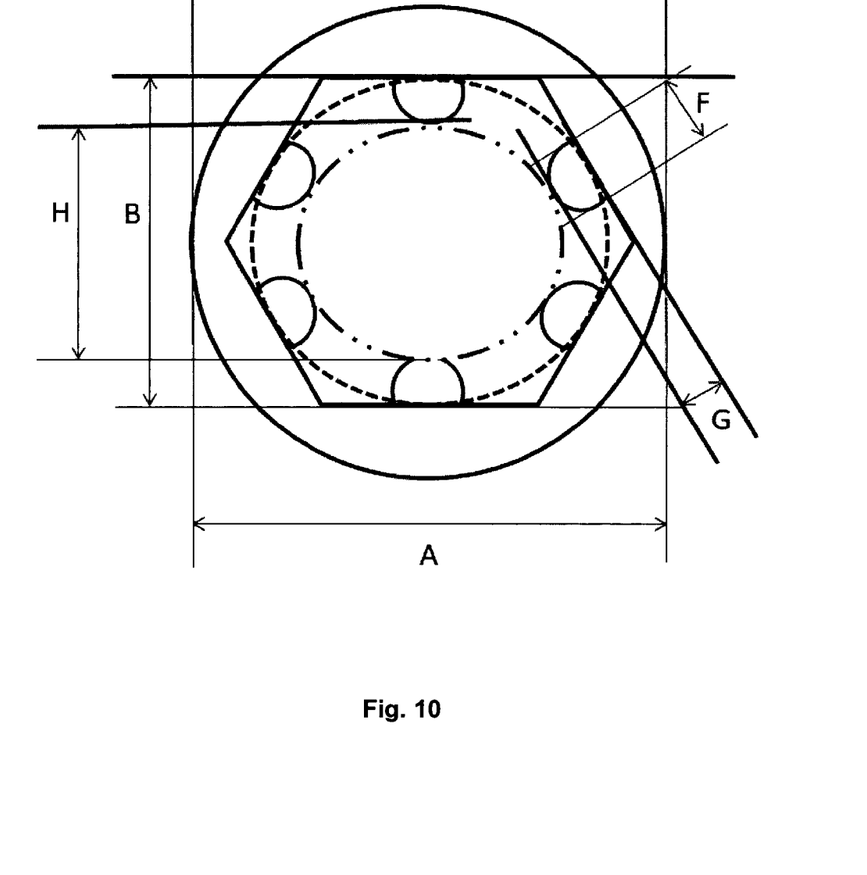

FIG. 10 shows the advantageous embodiment in which the internal polygonal drive is located deeper in the screw than the internal multilobular drive. The points of the internal multilobular drive are then not in a plane with the edges of the internal polygonal drive, but above them.

As shown, the internal polygonal drive here has a smaller diameter than the internal multilobular drive. The diameter for the internal multilobular drive is to be understood as the circle that is tangent to the points inside at its base (H). The diameter for the internal polygonal drive is to be understood as the circle which is tangent to all edges (B).

REFERENCE SIGNS

A Diameter of the screw head
B Diameter of the internal polygonal drive
C Depth of the screw drive
D Diameter of the screw shaft or thread diameter (outside)
E Total length of the screw
F Thickness of the torque protection points at the base
G Height of the torque protection points
G* Residual height of the points after breaking off
R Radius of the drilled hole in the points for weakening the maximum torque
H Diameter of the internal multilobular drive

The invention claimed is:
1. A screw having a screw drive, a screw shaft and a thread, the screw comprising:

two screw drives incorporated in a screw head, wherein a
first screw drive is an internal polygonal drive, and
a second screw drive is an internal multilobular drive,
wherein
the internal multilobular drive is a screw drive in the form of a multi-ray star including an internal polygonal drive, in which the rays are formed in torque protection points in the shape of rounded points or other shapes of the torque protection points, where the torque protection points lie in the same plane with the first screw drive,
a drilled hole formed in at least one of the torque protection points for weakening a maximum torque of the screw, and
the first and second screw drives comprise an integrated torque protection such that,
when the maximum torque is exceeded, the torque protection points enabling the drive break off, shear or are pressed flat to prevent damage to the thread and the screw shaft, or prevent the screw head from tearing off.

2. The screw having a screw drive according to claim 1, wherein
the internal multilobular drive is attached to the internal polygonal drive such that, after the torque protection points of the internal multilobular drive break off, shear or are pressed flat on account of the maximum torque being exceeded, the polygonal internal drive is preserved.

3. The screw having a screw drive according to claim 1 wherein
the internal polygonal drive is designed as an internal hexagonal drive or as an internal pentagonal drive or as an internal square drive or as an internal triangular drive.

4. The screw having a screw drive according to claim 1, wherein
a diameter of the internal polygonal drive (B) is 1-20 mm,
a depth of the screw drive (C) is 0.5-6 mm,
a thickness of the torque protection points at the base (F) is 0.1-4 mm,
a height of the torque protection points (G) is 0.1-3 mm,
a residual height of the torque protection points after breaking off (G*) is 0.01-1 mm,
and a diameter of the drilled hole formed in at least one of the torque protection points for weakening the maximum torque (2R) is 0.06-1.6 mm.

5. The screw having a screw drive according to claim 1, wherein
the first screw drive and second screw drive consist of at least one polymer or of wood or of ceramic or of composite or of at least one metal.

6. The screw having a screw drive according to claim 1, further comprising a biodegradable magnesium screw consisting of a magnesium alloy having a rare earth metal content of 1.5 to 5% by weight, preferably 1.5 to 2.5% by weight of neodymium, an yttrium content of 1.5 to 5% by weight, a zirconium content of 0.1 to 2.5% by weight, a zinc content of 0.01 to 1% by weight, as well as impurities, wherein the total content of impurities is below 1% by weight and the aluminium content is less than 0.5% by weight, and the remainder up to 100% by weight is magnesium.

7. The screw having a screw drive according to claim 6, wherein
a diameter of the screw head (A) is 2-30 mm,
a diameter of the internal polygonal drive (B) is 1-20 mm,
a depth of the screw drive (C) is 0.5-6 mm,
a diameter of the screw shaft/thread diameter (D) is 2-15 mm,
a total length of the screw (E) is 5-120 mm,
a thickness of the torque protection points at the base (F) is 0.1-4 mm,
a height of the torque protection points (G) is 0.1-3 mm,
a residual height of the torque protection points after breaking off (G*) is 0.01-1 mm, and
a diameter of the drilled hole in the torque protection points for weakening the maximum torque (2R) is 0.06-1.6 mm.

8. The screw having a screw drive according to claim 7, wherein said screw consists of at least one polymer or of wood or of wood or of ceramic or of composite or of at least one metal.

* * * * *